(12) United States Patent
Nishida (10) Patent No.: US 10,295,456 B2
(45) Date of Patent: May 21, 2019

(54) REMAINING LIFE ESTIMATION METHOD FOR ESTIMATING REMAINING LIFE OF HIGH-CHROMIUM STEEL PIPE

(71) Applicant: THE CHUGOKU ELECTRIC POWER CO., INC., Hiroshima (JP)

(72) Inventor: Hidetaka Nishida, Hiroshima (JP)

(73) Assignee: THE CHUGOKU ELECTRIC POWER CO., INC., Hiroshima (JP)

( * ) Notice: Subject to any disclaimer, the term of this patent is extended or adjusted under 35 U.S.C. 154(b) by 72 days.

(21) Appl. No.: 15/514,383

(22) PCT Filed: Oct. 1, 2014

(86) PCT No.: PCT/JP2014/076285
§ 371 (c)(1),
(2) Date: Mar. 24, 2017

(87) PCT Pub. No.: WO2016/051558
PCT Pub. Date: Apr. 7, 2016

(65) Prior Publication Data
US 2017/0292906 A1    Oct. 12, 2017

Related U.S. Application Data

(63) Continuation of application No. PCT/JP2014/076285, filed on Oct. 1, 2014.

(51) Int. Cl.
*G01N 17/00* (2006.01)
*G01N 3/08* (2006.01)
*G01N 3/18* (2006.01)

(52) U.S. Cl.
CPC .............. *G01N 17/006* (2013.01); *G01N 3/08* (2013.01); *G01N 3/18* (2013.01);
(Continued)

(58) Field of Classification Search
CPC .......... G01N 17/006; G01N 3/18; G01N 3/08; G01N 2203/0296; G01N 2203/0226; G01N 2203/0218; G01N 2203/0071
(Continued)

(56) References Cited

U.S. PATENT DOCUMENTS 5,275,893 A * 1/1994 Miyasaki .............. B32B 15/011
                                                    138/142
6,810,748 B1 * 11/2004 Nishida .................. G01N 33/20
                                                    356/32
(Continued)

FOREIGN PATENT DOCUMENTS

JP    2008-122345 A    5/2008
JP    4638621 B2       2/2011
(Continued)

OTHER PUBLICATIONS

Office Action issued in corresponding Canadian Application No. 2,962,544 dated Feb. 26, 2018 (5 pages).
(Continued)

*Primary Examiner* — Huy Q Phan
*Assistant Examiner* — Zannatul Ferdous
(74) *Attorney, Agent, or Firm* — Osha Liang LLP (57) ABSTRACT

An aspect of the present disclosure is to precisely define a constant value used in the Monkman-Grant analysis, when estimating remaining life of a high-chromium steel pipe through which high-temperature and high-pressure fluid is allowed to flow. A remaining life estimation method according to the present disclosure is particularly characterized in that a step of obtaining a constant on an accelerated creep test is performed in which a constant indicative of the product of a strain rate and a rupture time in the Monkman-Grant analysis is obtained by multiplying a first coefficient to transform uniaxial rupture ductility into multiaxial rupture
(Continued)

ductility, the uniaxial rupture ductility being obtained from a specimen of the high-chromium steel pipe, a second coefficient to amend consumed life of the specimen, and a third coefficient to amend a measured pressure into an assessment pressure.

4 Claims, 5 Drawing Sheets

(52) U.S. Cl.
CPC ............... *G01N 2203/0071* (2013.01); *G01N 2203/0218* (2013.01); *G01N 2203/0226* (2013.01); *G01N 2203/0296* (2013.01)

(58) Field of Classification Search
USPC .................................................. 73/760, 830
See application file for complete search history.

(56) References Cited

U.S. PATENT DOCUMENTS

| | | | | |
|---|---|---|---|---|
| 2006/0266448 | A1* | 11/2006 | Arai ..................... | C21D 1/18 148/593 |
| 2006/0283251 | A1* | 12/2006 | Hunaidi ................ | G01B 17/02 73/597 |
| 2007/0034301 | A1* | 2/2007 | Hasegawa ............. | C23C 8/32 148/318 |
| 2013/0214771 | A1* | 8/2013 | Tiernan ................ | G01N 27/904 324/242 |
| 2014/0092934 | A1* | 4/2014 | Isobe .................... | G01N 25/72 374/4 |
| 2014/0379280 | A1* | 12/2014 | Arai ..................... | G01N 3/40 702/34 |
| 2015/0276545 | A1* | 10/2015 | Takahashi ............ | G01M 3/243 73/592 |

FOREIGN PATENT DOCUMENTS

| | | |
|---|---|---|
| JP | 2013-117485 A | 6/2013 |
| JP | 2013-122411 A | 6/2013 |

OTHER PUBLICATIONS

Extended European Search Report issued in corresponding European Application No. 14903099.1 dated Sep. 18, 2017 (13 pages).
Wilson, Peter, "Remanent Creep Life Prediction in Low-Alloy Ferritic Steel Power Plant Components", Nov. 1, 1990, Univerisy of Cambridge (87 pages).
Jadaan, Osama M., "Deterministic Multiaxial Creep and Creep Rupture Enhancements for CARES/Creep Integrated Design Code", Jun. 1, 1998 (25 pages).
Seshadri, R. et al., "On Relating the Reference Stress, Limit Load and the ASME Stress Classification Concepts", International Journal of Pressure Vessels and Piping, vol. 56, No. 3, Jan. 1, 1993, pp. 387-408 (22 pages).
Prager, M., "Development of the MPC Omega Method for Life Assessment in the Creep Range", Journal of Pressure Vessel Technology, vo. 117, No. 2, May 1, 1995, pp. 95-103 (9 pages).

* cited by examiner

REMAINING LIFE ESTIMATION METHOD FOR ESTIMATING REMAINING LIFE OF HIGH-CHROMIUM STEEL PIPE

TECHNICAL FIELD

The present disclosure relates to a remaining life estimation method of estimating remaining life of a high-chromium steel pipe through which high-temperature and high-pressure fluid (e.g., steam for power) used for a boiler, etc., is allowed to flow.

BACKGROUND

Steam pipes are used for a boiler and a steam turbine in a power plant. Steam for power flowing through such a steam pipe includes, for example, high-temperature and high-pressure steam at a temperature of 280° C. or more at a pressure of 6 Mpa or more. At a thermal power plant, steam of a higher temperature and a higher pressure tends to be used to improve power generation efficiency.

A pipe for high-temperature and high-pressure fluid, such as a steam pipe, is subjected to high temperature and high pressure over a long period of time, and accordingly is under creep fatigue caused by heat stress. In order to improve endurance under creep fatigue, high-chromium steel (chromium-molybdenum steel having a higher chromium content rate than common steel) such as 9Cr steel or 12Cr steel is used suitably for a pipe. This pipe is formed such that plate-like base members made of high-chromium steel are curved in a circular shape and such base members are integrated by welding. However, in a weld portion in high-chromium steel, damage, such as a crack, hardly occurs until the end stage of its life, resulting in difficulty in estimating its remaining life.

Then, in a method described in Patent Literature 1, such remaining life is estimated using creep ductility and creep strain. Further, a method described in Patent Literature 2, a constant in the Monkman-Grant analysis is obtained using a steel pipe specimen imitating a high-chromium steel pipe.

CITATION LIST

Patent Literature

[PTL 1] Japanese Patent Application Laid-open Publication No. 2008-122345
[PTL 2] Japanese Patent Application Laid-open Publication No. 2013-117485

SUMMARY

Remaining life estimation using the Monkman-Grant analysis makes it possible to diagnose remaining life from an early stage. Since the method described in Patent Literature 2 uses a steel pipe specimen imitating a high-chromium steel pipe to obtain a constant, it proposes a useful method in estimating remaining life using the Monkman-Grant analysis. Here, in the remaining life estimation using the Monkman-Grant analysis, a constant value is extremely important.

One or more embodiments of the present invention precisely define a constant value used in the Monkman-Grant analysis.

One or more embodiments of the present invention provide a remaining life estimation method for estimating remaining life of high-chromium steel pipe through which high-temperature and high-pressure fluid is allowed to flow, the high-chromium steel pipe formed by integrating base members made of high-chromium steel by welding, the method comprising:
  an obtaining step of obtaining a constant indicating a product of a strain rate and a rapture time in Monkman-Grant analysis by multiplying
    a first coefficient to transform uniaxial rupture ductility into multiaxial rupture ductility, the uniaxial rupture ductility being obtained from a specimen of the high-chromium steel pipe,
    a second coefficient to amend consumed life of the specimen, and
    a third coefficient to amend a measurement pressure into an assessment pressure;
  a measuring step of measuring a strain of a surface of a steel pipe by measuring a distance between two points on an outer surface of the high-chromium steel pipe, using a sensor mounted to the outer surface of the high-chromium steel pipe on both sides of a welding material sandwiched therebetween;
  a recording step of recording strain information by recording, at a plurality of times, strain information indicating a strain of the outer surface of the steel pipe, in association with time information indicating a measurement time; and
  an estimating step of estimating remaining life of the high-chromium steel pipe, from the constant and a plurality of sets of the strain information and the time information.

According to one or more embodiments, a constant used in the Monkman-Grant analysis is obtained from uniaxial rupture ductility using first to third coefficients, at the step of obtaining a constant. Thus, the constant can be precisely defined.

In the above described remaining life estimation method, the measuring step may include
  measuring a distance between two points on the outer surface of the high-chromium steel pipe, using
    a base joined to the base member on one side sandwiching the welding material,
    a reflecting plate joined to an other side, and
    a laser displacement meter detachably mounted to the base, the laser displacement meter configured to apply a laser beam toward the reflecting plate, and receive reflected light from the reflecting plate.

In this method, measurement can be implemented with higher precision using the laser displacement meter.

In the above described remaining life estimation method, the estimating step may include
  estimating remaining life of the high-chromium steel pipe from the constant and a plurality of sets of the strain information and the time information, and,
  when the estimated remaining life corresponds to an end stage of life,
  calculating remaining life in accordance with an Omega method, using strain and strain-rate data correlating a strain and a strain rate from a plurality of sets of the strain information and the time information. In this method, when the Monkman-Grant analysis is used to estimate the remaining life to be in the end stage of life, the Omega method is used to calculate remaining life. Thus, it becomes possible to enhance the estimation accuracy of the remaining life in the end stage of life.

According to one or more embodiments of the present invention, it becomes possible to precisely define a constant to estimate remaining life of a high-chromium steel pipe through which high-temperature and high-pressure fluid is allowed to flow.

BRIEF DESCRIPTION OF DRAWINGS

FIGS. 2A and 2B are diagrams illustrating a measurement specimen and a laser displacement meter on an accelerated creep test.

DETAILED DESCRIPTION

Figure 1:
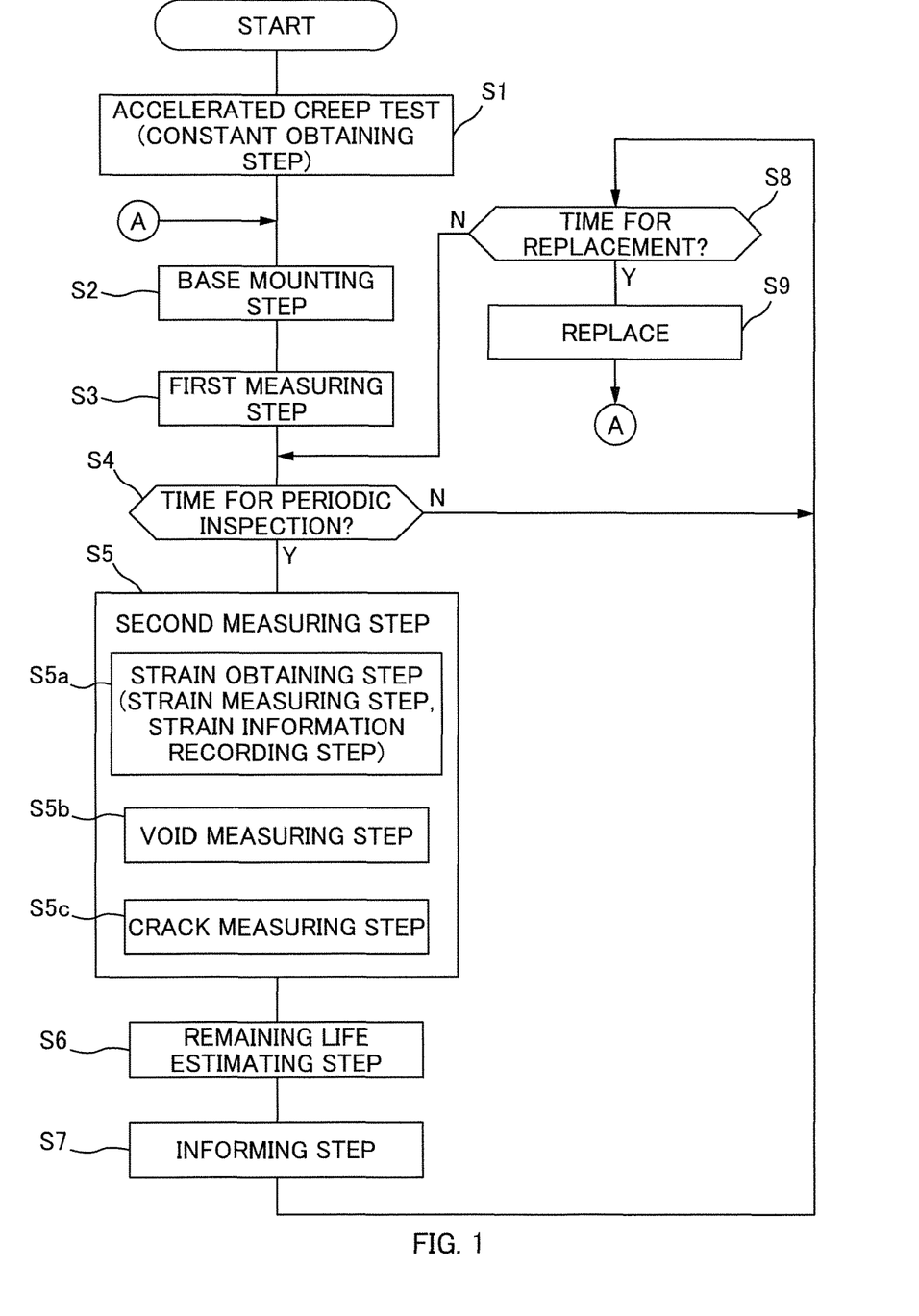
FIG. 1 is a flow chart illustrating a method of estimating remaining life.

Hereinafter, embodiments according to the present invention will be described with reference to the accompanying drawings. In a remaining life estimation method according to one or more embodiments, as illustrated in FIG. 1, an accelerated creep test (S1), a base mounting step (S2), a first measuring step (S3), a second measuring step (S5), a remaining life estimating step (S6), an informing step (S7), and a replacing step (S9) are performed.

The outline of the remaining life estimation method will be described. In this remaining life estimation method, firstly, measurements are made on the accelerated creep test (S1) using a specimen of a high-chromium steel pipe (which will be described later). That is, the specimen is subjected to a test environment in which temperature and pressure are set at test temperature and test pressure, respectively, heating and pressurization of the specimen are stopped every time a specified time period elapses, and a strain, a creep void, etc., are measured. Then, from such obtained measurement values, a constant and a parameter L, etc., which are used in the Monkman-Grant analysis, are obtained. Thus, this accelerated creep test corresponds to a constant obtaining step.

Next, in the base mounting step (S2), a base and a reflecting plate are mounted to a high-chromium steel pipe to be measured. This base is configured to be detachably attached with a laser displacement meter, which will be described later. The reflecting plate is configured to reflect a laser beam applied from the laser displacement meter, toward the laser displacement meter. After the base has been mounted, a distance of a predetermined interval, a creep void, and a crack formed in the interior in the initial state in the high-chromium steel pipe are measured at the first measuring step (S3). After the various initial values are measured, it is determined whether the time for periodic inspection has been reached (S4). When the time for periodic inspection has been reached, the step is shifted to the second measuring step (S5). In this second measuring step, a strain obtaining step (S5a), a void measuring step (S5b), and a crack measuring step (5c) are performed.

In the strain obtaining step at the step S5a, a distance of the predetermined interval in the high-chromium steel pipe at the time of periodic inspection is measured using the laser displacement meter that is mounted to the base. The information of such a measured distance is recorded with the information of the measurement date and time. The distance measured at this step represents a strain in the high-chromium steel pipe. Thus, the strain obtaining step at the step S5a corresponds to a strain measuring step and a strain information recording step according to one or more embodiments of the present invention. In the void measuring step at the step S5b, a creep void formed near a weld portion in the high-chromium steel pipe is measured. Then, such measurement results (location, area, number, etc., of creep void(s)) are recorded with the time information. In the crack measuring step at the step S5c, ultrasonic crack detection of a boundary portion between a base member and a welding material in the high-chromium steel pipe is performed by a phased array ultrasonic crack detector. Then, such measurement results (the height, length, location, etc., of a crack) are recorded with the time information.

In the remaining life estimating step (S6), first, the remaining life of the high-chromium steel pipe is estimated in accordance with the Monkman-Grant analysis. At this time, the constant obtained on the accelerated creep test at the step S1 and a plurality of sets of the strain information and the time information are used. Then, when the remaining life estimated in accordance with the Monkman-Grant analysis indicates the end stage of the life of the high-chromium steel pipe, the remaining life is estimated based on the Omega method. That is, strain and strain-rate data (see FIG. 6) correlating a strain with a strain rate is used to calculate the remaining life in accordance with the Omega method. Further, even in a case where the remaining life estimated in accordance with the Monkman-Grant analysis does not indicate the end stage of the life of the high-chromium steel pipe, the remaining life is estimated based on the Omega method, if at least one of a parameter L, a void number density, and remaining life obtained by applying crack information to a master curve, indicates the end stage of the life of the high-chromium steel pipe.

In the informing step (S7), the remaining life estimated at the remaining life estimating step is informed, for example, by being displayed on a display of a computer system, being printed on paper, or the like. It should be noted that when the remaining life calculated using the Monkman-Grant analysis is amended into the remaining life calculated using other methods, the amended remaining life is to be informed with the information indicative of the end stage of the life (message, etc.).

When it is determined that the time for periodic inspection has not been reached at the step S4, or the remaining life has been informed at the step S7, it is determined whether the time for displacing the high-chromium steel pipe has been reached (S8). Then, when the time for such displacement has been reached, the high-chromium steel pipe is replaced with a new pipe at the replacing step (S9). Thereafter, at the step S2, processes at and after the base mounting step are to be repeatedly performed. Whereas, when the time for displacement has not been reached, it is determined whether the time for periodic inspection has been reached at the step S4.

Next, the characteristics of the remaining life estimation method will be described. In this remaining life estimation method, since the accelerated creep test (S1) has a special feature, description will be made focusing on the acceleration test.

Figure 2A:
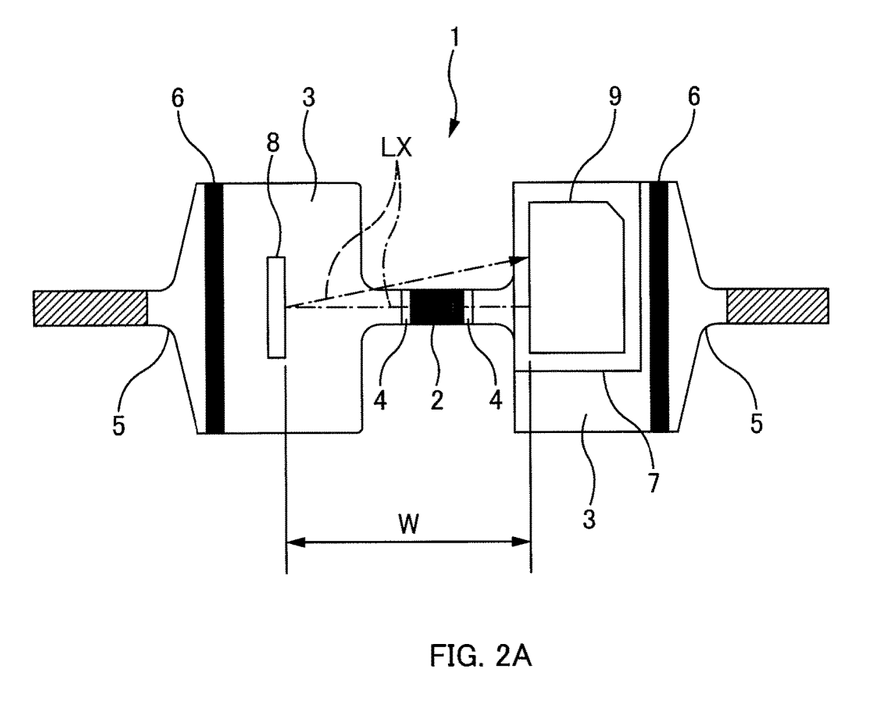
FIG. 2A is a diagram seen from a planar direction.
Figure 2B:
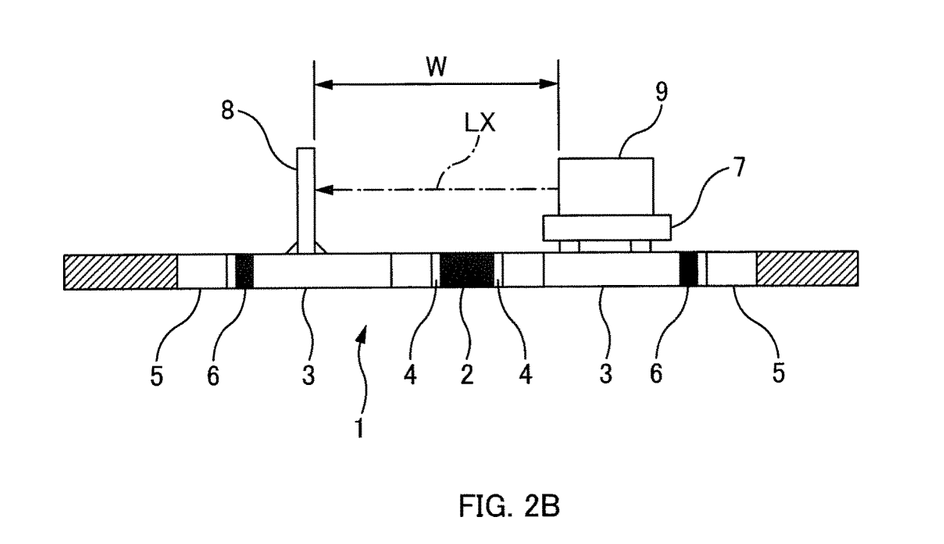
FIG. 2B is a diagram seen from a lateral direction.

On the accelerated creep test (S1), a specimen of the high-chromium steel pipe is used. This specimen is cut out from a steam pipe that has been used for high-temperature and high-pressure steam to flow therethrough at power generation facilities and replaced. Thus, the time period during which the pipe is used until its replacement is known. As illustrated in FIGS. 2A and 2B, such a specimen 1 is cut out such that base members 3 are positioned on both sides of a welding material 2 sandwiched therebetween. That is, the specimen 1 is cut out such that the corresponding base members 3 are each in a substantially rectangular shape in plan view, and the welding material 2 and a heat-affected zone 4 are in a prismatic shape. Further, metal support portions 5 are respectively welded to edge portions, in the base members 3, on the side opposite to the welding material 2. It should be noted that members each denoted by a reference numeral 6 in FIGS. 2A and 2B are welding materials for welding the support portions 5 and the base members 3, respectively.

Further, while the welding material 2 is sandwiched, a base 7 is welded to a surface of the base member 3 on one side and a reflecting plate 8 is welded to a surface of the base member 3 on the other side. The base 7 is an object to which the laser displacement meter 9 is to be detachably mounted. The base 7 is made of the same metal material as that of a base 17 that is welded to target high-chromium steel in the base mounting step (S2), and they are of the same shape. The reflecting plate 8 is a metal plate member configured to reflect a laser beam LX applied from the laser displacement meter 9, toward the laser displacement meter 9. This reflecting plate 8 is also made of the same metal material as that of a reflecting plate 18 that is welded in the base mounting step, and they are of the same shape. A distance W between the base 7 (laser displacement meter 9) and the reflecting plate 8 is set at a specified value, and the distance W is set at the same value also in the base mounting step which will be described later.

When the base 7 and the reflecting plate 8 have been mounted, measurements at the starting point of the acceleration test are performed. Here, the laser displacement meter 9 is mounted to the base 7, and a distance of the predetermined interval to the reflecting plate 8 is measured. Further, a creep void and a crack formed the inside are also measured with respect to this specimen 1. A creep void is measured, for example, such that a replica is taken from the outer surface of the specimen 1 and this replica is measured by being observed with a microscope. Further, a crack is measured, for example, such that the specimen 1 is subjected to ultrasonic crack detection.

When the measurements at the starting point have been performed, the specimen 1 is heated and pressurized. Here, the specimen is disposed in a furnace in such a state that tensile strength of predetermined stress is applied to the support portions 5 on both sides. Thereafter, the temperature in the furnace is adjusted to a predetermined temperature. When this state has been maintained for a specified time period, heating and pressurization are temporarily stopped. That is, the temperature in the furnace is lowered, and the specimen 1 is taken out. Then, with respect to the taken-out specimen 1, a distance measurement is performed using the laser displacement meter 9, a creep void measurement is performed using a replica, and a measurement of a crack formed the inside is performed through ultrasonic crack detection. Thereafter, such measurement values are recorded, as the measurement values at the first temporary stop, with the information of elapsed time.

When the measurement values at the first temporary stop have been recorded, the specimen 1 is heated and pressurized again. Here, also, the specimen 1 in a state of being applied with the tensile strength of the predetermined stress is disposed in the furnace, and thereafter, the temperature in the furnace is adjusted to a predetermined temperature. When this state has been maintained for a specified time period, the second temporary stop is made, and the measurement values at the second temporary stop are recorded with the information of elapsed time, similarly to the first stop. Thereafter, the specimen 1 is heated and pressurized, and measured, repeatedly, until the specimen 1 is ruptured. Accordingly, the measurement values at and after the third temporary stop are recorded.

When this specimen 1 has been heated and measured repeatedly until the specimen 1 is ruptured, a constant used in the Monkman-Grant analysis, that is, a constant representing the product of a strain rate and a rupture time, is calculated. As given in an expression (1), the constant is calculated using uniaxial rupture ductility and first to third coefficients.

$$\text{Constant } X = \text{Uniaxial rupture ductility } CR \times \text{First coefficient} \times \text{Second coefficient} \times \text{Third coefficient} \qquad (1)$$

In the expression (1), uniaxial rupture ductility is obtained by measurement on the accelerated creep test. The first coefficient is to transform uniaxial rupture ductility into multiaxial rupture ductility. The second coefficient is to amend consumed life of the specimen 1. The third coefficient is to amend measured pressure into assessment pressure.

Figure 3:
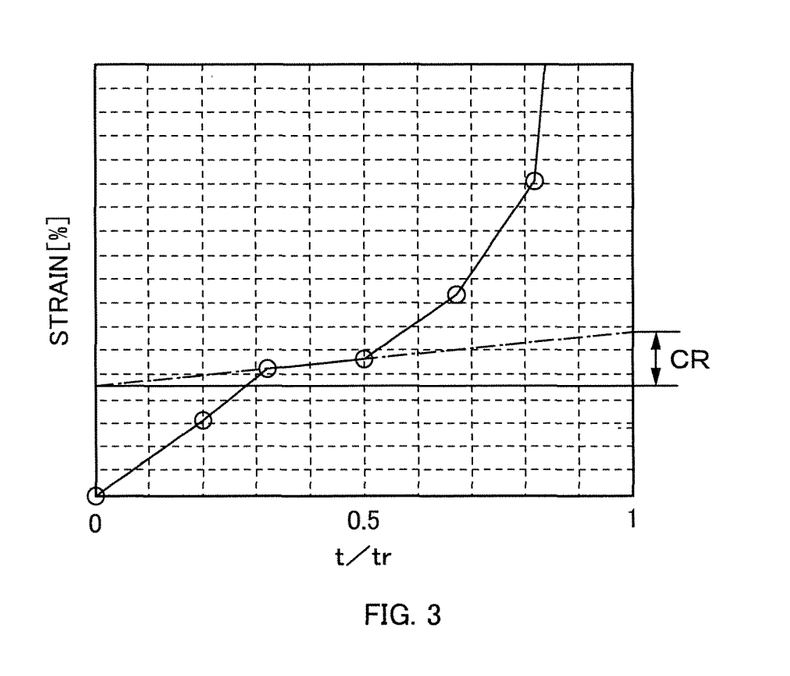
FIG. 3 is a diagram illustrating relationship between strain and creep life consumption rate (t/tr) on an accelerated creep test.

Uniaxial rupture ductility is obtained based on a distance measured using the laser displacement meter 9, that is, a distance of the predetermined interval defined by joint positions of the base 7 and the reflecting plate 8. Here, FIG. 3 is a diagram illustrating relationship between a strain and a creep life consumption rate (t/tr) on the accelerated creep test, where a horizontal axis represents a creep life consumption rate of the specimen 1, while a vertical axis represents a strain. In the creep life consumption rate, the starting point of the acceleration test is set at 0, while the rupture point is set at 1. Further, a strain is calculated, with a distance at the starting point of the acceleration test being used as a standard. In an example of FIG. 3, a set of a strain and a creep life consumption rate is linearly approximated, to obtain CR [%] as rupture ductility.

The first coefficient is, as has been described, a coefficient to transform uniaxial rupture ductility into multiaxial rupture ductility. This first coefficient is calculated based on von Misses equivalent stress and hydrostatic stress and is set at, for example, 0.5.

The second coefficient is, as has been described, a coefficient to amend the consumed life of the specimen 1. This second coefficient is determined, based on a time period during which the high-chromium steel pipe constituting the specimen 1 was actually used, and test time of this acceleration test (a time period from the start of the test to rupture). For example, in consideration of test temperature and test pressure at the acceleration test, the test time under usage environment of the high-chromium steel pipe is calculated. Then, from such a calculated test time and the actual test time, a rupture time required for rupture and the ratio of the test time relative to the rupture time is calculated. Further, the second coefficient is calculated from the ratio of the test time to the rupture time. For example, in a case where the test time is 0.2 when the rupture time is set at 1, the second coefficient results in $1/0.2=5$.

The third coefficient is, as has been described, a coefficient to amend measured pressure into assessment pressure. This third coefficient is calculated from relationship between test stress and limit strain. Here, FIG. 4 is a diagram illustrating relationship between test stress and limit strain.

Figure 4:
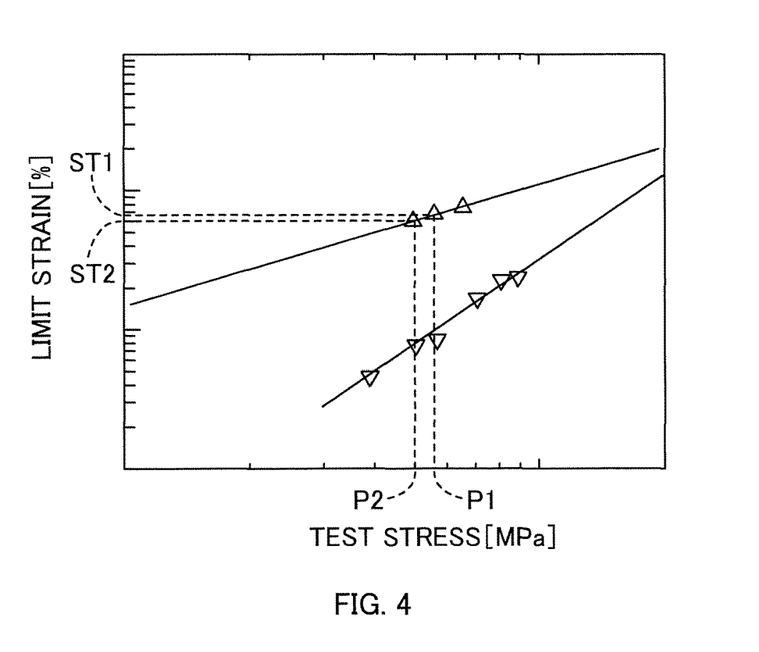
FIG. 4 is a diagram illustrating relationship between test stress and limit strain.

In FIG. 4, the horizontal axis represents a test stress [MPa], while the vertical axis represents a limit strain [%]. Then, the points each indicated by a symbol of an upward triangle are the measurement points of 9Cr steel, while the points each indicated by a symbol of a downward triangle are measurement points of 12Cr steel.

Measurement points of the same kind of metal are subjected to first order approximation, to obtain a primary expression expressing relationship between test stress and limit strain in each metal. Then, the obtained primary expression is used to obtain a limit strain corresponding to an assessment pressure. Further, the third coefficient is obtained from a limit strain corresponding to a test stress and a limit strain corresponding to an assessment pressure. For example, in a case where a limit strain ST1 corresponding to a test stress P1 is 0.65% and a limit strain ST2 corresponding to an assessment pressure P2 is 0.60%, the third coefficient results in 0.60%/0.65%=0.92.

Figure 5:
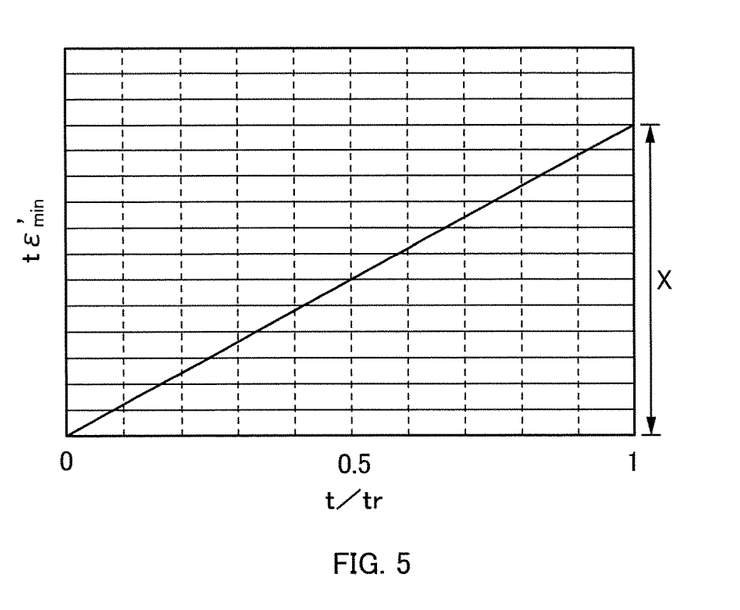
FIG. 5 is a diagram illustrating relationship (master curve) between creep life consumption rate (t/tr) and the product of operating time and creep strain rate ($t \cdot \varepsilon'_{min}$).

When the constant X used in the Monkman-Grant analysis has been obtained based on the expression (1), a master curve is created. Here, FIG. 5 illustrates an example of relationship (master curve) between a creep life consumption rate (t/tr) and the product of a used time and a creep strain rate ($t \cdot \varepsilon'_{min}$). As illustrated in FIG. 5, the product of the used time and the creep strain rate ($t \cdot \varepsilon'_{min}$) when the creep life consumption rate is 1 corresponds to the constant X.

It should be noted that this constant X may be obtained using not only such a specimen 1 that a weld portion is cut out from the replaced high-chromium steel pipe, as in one or more embodiments, but also a steel pipe specimen imitating the high-chromium steel pipe.

Figure 6:
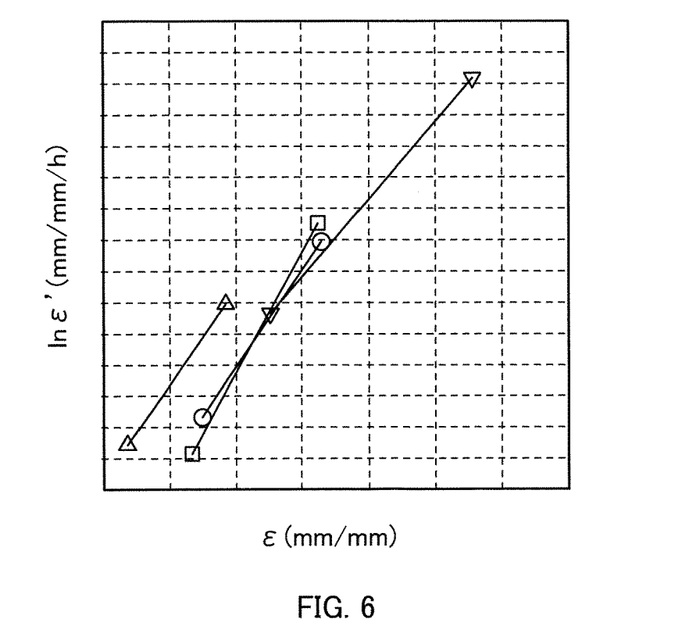
FIG. 6 is a diagram illustrating relationship between strain rate and strain used in the Omega method.

Further, in the accelerated creep test (S1), assessment standard in the Omega method is created based on the measurement results. Here, the Omega method is such a law that the product of the gradient ($\Omega$) of creep strain rate relative to strain, creep strain rate, and remaining life is always constant. Accordingly, more than two sets of creep strain rate information are used to delete the constant of the Omega method, and the remaining life can be estimated. In this Omega method, the gradient of creep strain rate relative to strain is used. Thus, as illustrated in FIG. 6, strain is plotted on the horizontal axis and creep strain rate is plotted on the vertical axis, to obtain such a gradient.

Figure 7:
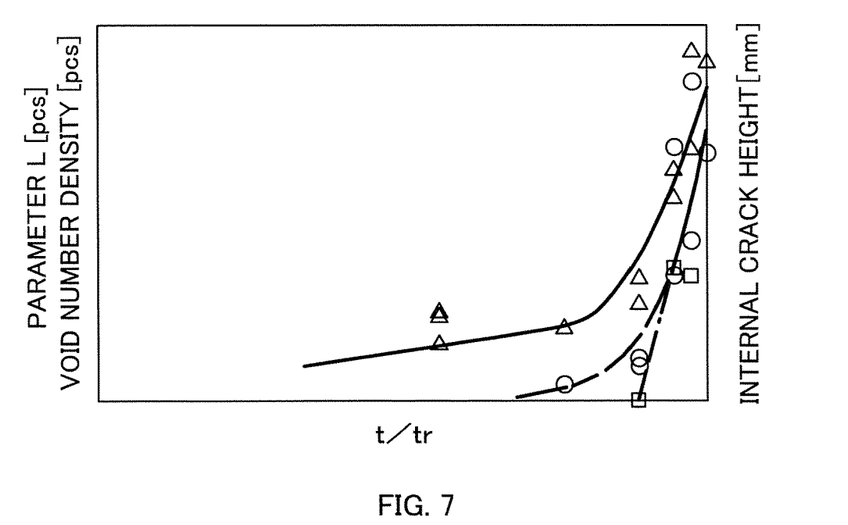
FIG. 7 is a diagram illustrating a master curve used in another method.

In addition, in this accelerated creep test (S1), as illustrated in FIG. 7, a master curve of parameter L (void connection density parameter) and void number density is also created, based on information of a creep void obtained from measurements. Further, a master curve of crack height (depth) is created based on crack information obtained from measurements.

Next, the base mounting step (S2) will be described. In the base mounting step, the base 17 and the reflecting plate 18 are joined to the high-chromium steel pipe 11 that is a measurement target. This base 17 is, as described in the accelerated creep test at the step S1, an object to which the laser displacement meter 9 is to be detachably mounted. Further, the reflecting plate 18 is a metal plate member configured to reflect the laser beam LX applied from the laser displacement meter 9, toward the laser displacement meter 9.

Figure 8:
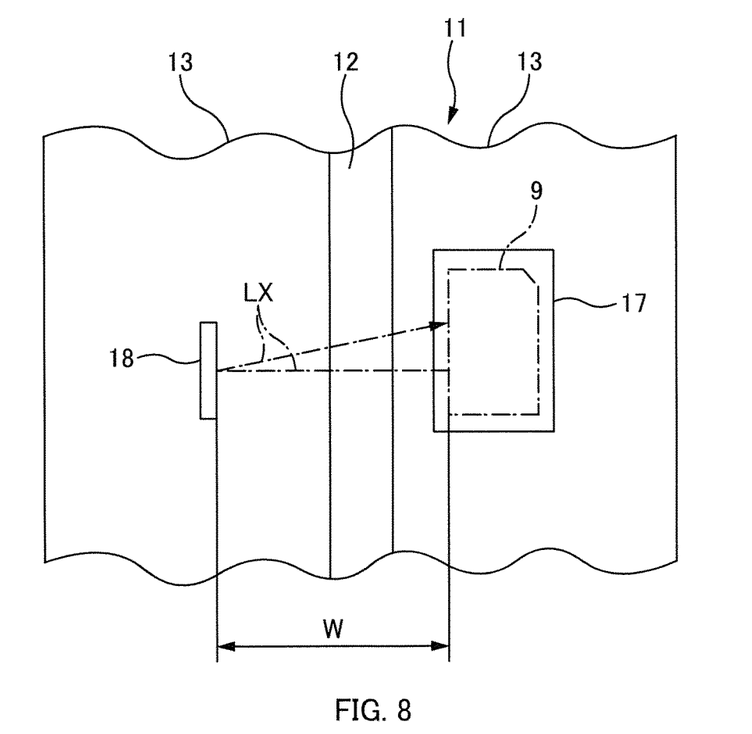
FIG. 8 is a diagram illustrating an aspect in which a laser displacement meter is mounted at a time of periodic inspection.

When the base 17 and the reflecting plate 18 are joined to an outer surface of the high-chromium steel pipe 11, as illustrated in FIG. 8, the base 17 is joined by welding to a base member 13 on one side sandwiching a welding material 12. Similarly, the reflecting plate 18 is joined by welding to the base member 13 on the other side sandwiching the welding material 2. That is, the reflecting plate 18 and the laser displacement meter 9 mounted to the base 17 are mounted to the base members 13, 13 on both sides of the welding material 12 sandwiched therebetween. At such a time, a distance W of a predetermined interval between the laser displacement meter 9 and the reflecting plate 18 is set at the distance W of the predetermined interval as in the specimen 1.

Thereafter, the steps described above are performed. Briefly explaining this, various initial values are measured at the first measuring step (S3), and a distance of the predetermined interval, a creep void, a crack formed the inside are measured at the second measuring step (S5) every time the periodic inspection time is reached (S5a to S5c). Further, at the remaining life estimating step (S6), the remaining life of the high-chromium steel pipe 11 is estimated in accordance with the Monkman-Grant analysis. In addition, parameter L, void number density, and remaining life based on crack information are also estimated. Then, when at least one of the remaining lifes estimated using the methods indicates the end stage of the life of the high-chromium steel pipe 11, the remaining life estimation is performed based on the Omega method. When the remaining life has been estimated, the remaining life is informed at the informing step (S7). Based on the informed remaining life, the time for displacement of the high-chromium steel pipe 11 is determined (S8). When it is determined that the time for displacement has been reached, the high-chromium steel pipe 11 is replaced with a new one at the replacing step (S9).

As understood from the above description, according to the remaining life estimation method of one or more embodiments, the first coefficient to transform uniaxial rupture ductility, obtained from the specimen 1 of the high-chromium steel pipe, into multiaxial rupture ductility, the second coefficient to amend the consumed life of the specimen 1, and the third coefficient to amend measurement pressure into assessment pressure, are multiplied to obtain the constant X indicating the product of strain rate and rupture time in the Monkman-Grant analysis, on the accelerated creep test (constant obtaining step) at the step S1. Therefore, the constant X can be precisely defined.

Further, in the accelerated creep test at the step S1 and in the second measuring step (strain measuring step) at the step S5, the base 7, 17, which is joined to the base member 3, 13 on one side sandwiching the welding material 2, 12, the reflecting plate 8, 18, which is joined to the base member 3, 13 on the other side, and the laser displacement meter 9, which is detachably mounted to the base 7, 17 and is configured to apply the laser beam LX toward the reflecting plate 8, 18 and receive the reflected light from the reflecting plate 8, 18 are used, to measure a distance between two points on the outer surface of the specimen 1 or the high-chromium steel pipe 11. Thus, measurements with higher precision using the laser displacement meter 9 can be implemented.

Further, in the remaining life estimating step at the step S6, the remaining life of the high-chromium steel pipe 11 is estimated from the constant and a plurality of sets of strain information and time information. Also, when the estimated remaining life is the time period corresponding to the end stage of the life, strain and strain-rate data correlating strain with strain rate from a plurality of sets of strain information and time information is used to calculate the remaining life in accordance with the Omega method. Thus, the estimation accuracy of the remaining life in the end stage of the life can be improved.

It should be noted that, one or more embodiments described above are provided to facilitate the understanding of the present disclosure, and it is not in any way to be construed as limiting the invention. The present disclosure may be changed and altered without departing from the gist thereof, and encompass equivalents thereof.

For example, in one or more embodiments describe above, steam for power is given as an example of high-temperature and high-pressure fluid. However, as long as a pipe is a high-chromium steel pipe through which fluid of temperature and pressure equivalent to those of steam for power is allowed to flow, one or more embodiments of the present invention can be applied similarly.

Further, in one or more embodiments describe above, the laser displacement meter 9 is given as an example of a device configured to measure surface strain of the high-chromium steel pipe 11. However, as long as a device is capable of measuring surface strain, other devices may be used. For example, resistive strain sensor or capacitance type strain sensor may be used. In this case also, a sensor is mounted to the base members 13 on both sides of the welding material 12 sandwiched therebetween.

Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

REFERENCE SIGNS LIST

1 . . . specimen of high-chromium steel pipe
2 . . . welding material
3 . . . base member
4 . . . heat-affected zone
5 . . . support portion
6 . . . welding material
7 . . . base
8 . . . reflecting plate
9 . . . laser displacement meter
11 . . . high-chromium steel pipe
12 . . . welding material
13 . . . base member
17 . . . base
18 . . . reflecting plate
LX . . . laser beam
W . . . distance between base (laser displacement meter) and reflecting plate

The invention claimed is:

1. A remaining life estimation method for estimating remaining life of high-chromium steel pipe through which high-temperature and high-pressure fluid is allowed to flow, the high-chromium steel pipe formed by integrating base members made of high-chromium steel by welding, the method comprising:
  obtaining a constant indicating a product of a strain rate and a rapture time in Monkman-Grant analysis by multiplying
    a first coefficient to transform uniaxial rupture ductility into multiaxial rupture ductility, the uniaxial rupture ductility being obtained from a specimen of the high-chromium steel pipe,
    a second coefficient to amend consumed life of the specimen, and
    a third coefficient to amend a measurement pressure into an assessment pressure;
  measuring a strain of an outer surface of the high-chromium steel pipe by measuring a distance between two points on the outer surface of the high-chromium steel pipe, using a sensor mounted to the outer surface of the high-chromium steel pipe on both sides of a welding material sandwiched therebetween;
  recording strain information by recording, at a plurality of times, the strain information indicating the strain of the outer surface of the high-chromium steel pipe, in association with time information indicating a measurement time; and
  estimating remaining life of the high-chromium steel pipe, from the constant and a plurality of sets of the strain information and the time information.

2. The remaining life estimation method according to claim 1, wherein the measuring of the strain comprises:
  measuring the distance between the two points on the outer surface of the high-chromium steel pipe, using
    a base joined to the base member on a first side sandwiching the welding material,
    a reflecting plate joined to a second side, and
    a laser displacement meter detachably mounted to the base, the laser displacement meter applies a laser beam toward the reflecting plate, and receives reflected light from the reflecting plate.

3. The remaining life estimation method according to claim 1, wherein
  the estimating of the remaining life comprises:
    estimating remaining life of the high-chromium steel pipe from the constant and a plurality of sets of the strain information and the time information, and,
    when the estimated remaining life corresponds to an end stage of life,
    calculating remaining life in accordance with an Omega method, using strain and strain-rate data correlating the strain and the strain rate from a plurality of sets of the strain information and the time information.

4. The remaining life estimation method according to claim 2, wherein the estimating of the remaining life comprises:
  estimating remaining life of the high-chromium steel pipe from the constant and a plurality of sets of the strain information and the time information, and,
  when the estimated remaining life corresponds to an end stage of life,
  calculating remaining life in accordance with an Omega method, using strain and strain-rate data correlating the strain and the strain rate from a plurality of sets of the strain information and the time information.

* * * * *